United States Patent [19]

Theeuwes

[11] Patent Number: 4,511,351
[45] Date of Patent: Apr. 16, 1985

[54] PARENTERAL DELIVERY SYSTEM UTILIZING A HOLLOW FIBER CELLULAR UNIT

[75] Inventor: Felix Theeuwes, Los Altos, Calif.
[73] Assignee: ALZA Corporation, Palo Alto, Calif.
[21] Appl. No.: 609,592
[22] Filed: May 14, 1984
[51] Int. Cl.³ .............................................. A61M 5/14
[52] U.S. Cl. ..................................... 604/56; 604/85; 604/92; 604/246
[58] Field of Search ..................................... 604/80–85, 604/56, 892, 92, 246, 251, 257; 424/19, 21

[56] References Cited

U.S. PATENT DOCUMENTS

| | | |
|---|---|---|
| 2,954,028 | 9/1960 | Smith . |
| 3,001,525 | 9/1961 | Hendricks . |
| 3,305,446 | 2/1967 | Bechtol et al. ........................ 167/72 |
| 3,322,114 | 5/1967 | Portnoy et al. . |
| 3,756,237 | 9/1973 | Chittenden et al. . |
| 3,756,390 | 9/1973 | Abbey et al. ...................... 206/47 A |
| 3,760,984 | 9/1973 | Theeuwes ............................ 222/95 |
| 3,797,485 | 3/1974 | Urquhart . |
| 3,797,494 | 3/1974 | Zaffaroni . |
| 3,845,770 | 11/1974 | Theeuwes et al. . |
| 3,848,603 | 11/1974 | Throner . |
| 3,854,480 | 12/1974 | Zaffaroni . |
| 3,921,635 | 11/1975 | Gauthier . |
| 3,921,636 | 11/1975 | Zaffaroni . |
| 3,941,126 | 3/1976 | Dietrick et al. . |
| 3,948,254 | 4/1976 | Zaffaroni . |
| 3,976,068 | 8/1976 | Lindquist . |
| 3,993,072 | 11/1976 | Zaffaroni . |
| 3,993,073 | 11/1976 | Zaffaroni . |
| 3,995,631 | 12/1976 | Higuchi et al. . |
| 4,061,141 | 12/1977 | Hydes . |
| 4,177,256 | 12/1979 | Michaels et al. ....................... 424/22 |
| 4,203,439 | 5/1980 | Theeuwes . |
| 4,217,894 | 8/1980 | Franetzki . |
| 4,233,973 | 11/1980 | Shulka . |
| 4,256,104 | 3/1981 | Muetterties et al. . |
| 4,323,457 | 4/1982 | Sun et al. ............................ 210/645 |

FOREIGN PATENT DOCUMENTS 497181  9/1969  Switzerland .
982107  9/1963  United Kingdom .

OTHER PUBLICATIONS

Paxinos, J. and Samuels, T. M.; *Am. J. Hosp. Pharm.*, vol. 32, pp. 892–897, Sep. 1975.
Goodwin, H. N., *The American Journal of I. V. Therapy*, pp. 27–30, Dec.–Jan. 1975.
Masson, A. H. B., *Brit. J. Anaesth.*, vol. 43, pp. 681–686, (1971).
Ferenchak et al., *Surgery*, vol. 70, No. 5, pp. 674–677, Nov., 1971.

*Primary Examiner*—Stephen C. Pellegrino
*Attorney, Agent, or Firm*—Paul L. Sabatine; Edward L. Mandell; Steven F. Stone

[57] ABSTRACT

A formulation cell consisting essentially of a hollow fiber surrounded by a beneficial agent is disclosed for use in an intravenous delivery system. An intravenous system is disclosed that uses the formulation cell.

5 Claims, 6 Drawing Figures

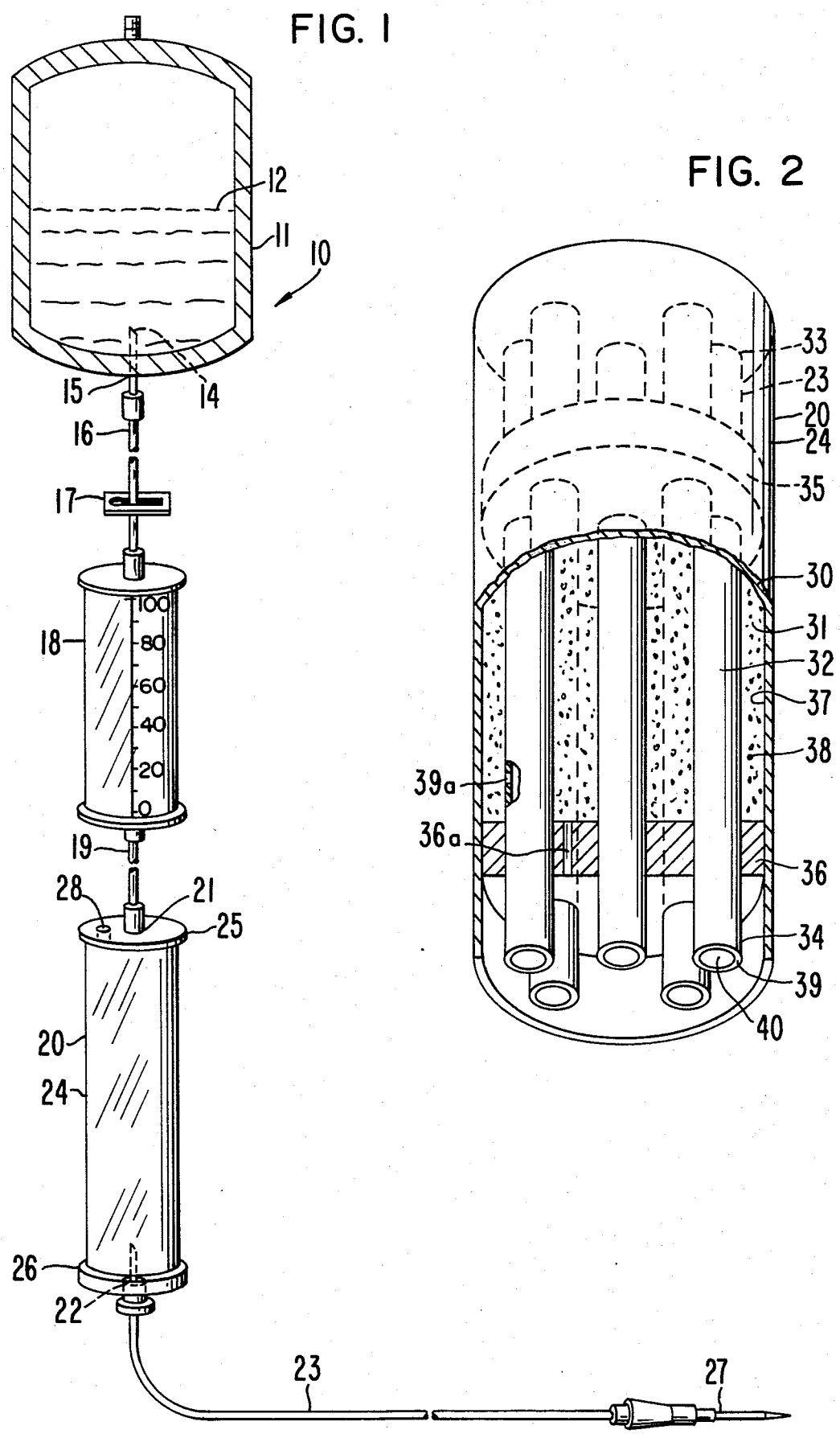

PARENTERAL DELIVERY SYSTEM UTILIZING A HOLLOW FIBER CELLULAR UNIT

FIELD OF THE INVENTION

This invention pertains to a parenteral delivery system. The delivery system comprises a reservoir containing a parenterally administrable fluid, a drip chamber and a cellular unit. The unit houses at least one hollow fiber that is surrounded in at least a part of the exterior area occupied by the hollow fiber by a parenterally administrable beneficial agent. The parenteral delivery system is useful for administering a beneficial active agent to a recipient.

BACKGROUND OF THE INVENTION

The parenteral administration of beneficial agents to a needy recipient is a well-accepted and established clinical practice. Presently, a beneficial agent often is administered by using a parenteral delivery system. The parenteral delivery system comprises a formulation chamber containing an active agent, that is mixed with an incoming parenterally administrable fluid to form an administrable fluid agent formulation. The fluid is supplied from a fluid container suspended above the formulation chamber. While the form of parenteral administration is widely used and can lead to acceptable therapy, there is still a great deal of dissatisfaction with this kind of delivery system that lends itself to improvement. Mainly, the value of the system can be improved and its therapeutic usefulness increased if (1) a means and method are made available for governing the rate of introduction of active agent into an intravenous fluid; and, (2) a means and method are made available for governing the rate of introduction of active agent into an intravenous fluid coupled with means for controlling the flow rate of the fluid agent formulation to a recipient.

DESCRIPTION OF THE INVENTION

It is immediately apparent, in view of the above written discussion, that a critical need exists for a parenteral delivery system that overcomes the dissatisfaction associated with the prior art. The invention of this application provides a practical and useful solution to the above problem. That is, this invention makes available a parenteral delivery system comprising; (1) a formulation cellular unit housing a hollow fiber, or a hollow fiber, arrangement that is a means for introducing a beneficial agent into a medical fluid, and which parenteral delivery system also is; (2) a means for governing the fluid flow rate of the fluid agent formulation to a recipient. The delivery system delivers a beneficially effective amount of beneficial agent by the combined operation of the hollow fiber providing a means for releasing a beneficial intravenously agent and by the rate of flow of intravenously administrable fluid through the cellular unit.

BRIEF DESCRIPTION OF THE DRAWINGS

FIG. 1 is a perspective view of a parenteral delivery system provided by the invention;

FIG. 2 is an opened view of a cellular unit housing a plurality of hollow fibers and a beneficial active agent as provided by the invention;

Figure 3:
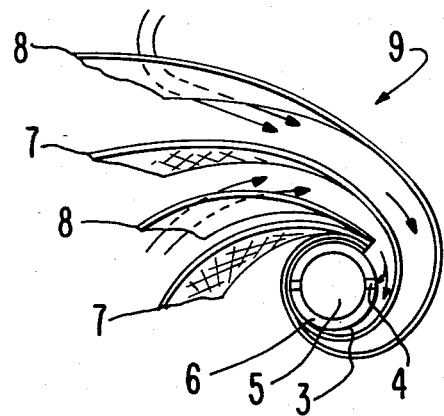
FIG. 3 is an exploded view of a spiral wound module for use in the cellular unit.

The accompanying drawing figures are not drawn to scale but they are set forth to illustrate various embodiments and structural parameters of the invention. In the drawing figures and in the specification, like parts in related drawing figures are identified by like numbers. The terms appearing earlier in the specification are described hereinafter.

DETAILED DESCRIPTION OF THE DRAWING FIGURES

FIG. 1 represents a parenteral delivery system 10 provided by the invention and designated by the numeral 10. Parenteral delivery system 10 of FIG. 1 comprises a reservoir container 11 of a medical fluid 12 acceptable for parenteral administration including intravenous administration. Reservoir 11, in the illustrated embodiment is a container made of plastic and it is understood the container can be made of other acceptable materials such as glass. Reservoir 11 in the embodiment made of plastic comprises a flexible, or a semi-rigid, preferably transparent material such as a non-toxic polyolefin, polyvinyl chloride, or the like. Reservoir 11 is connected to the rest of delivery system 10 through connecting spike 14. Spike 14 is hollow and it pierces plastic bag 11 at end. The other end of spike 15 is connected to a section of medical grade tube 16 that passes through a flow regulator clamp 17 and enters a drip chamber 18. Spike 15 and tube 16 convey medical fluid 12 into drip chamber 18 wherein it proceeds dropwise in said drip chamber 18.

Medical fluid 12 is typically a sterile solution, such as a solution of dextrose, a solution of an electrolyte, or saline. Medical fluid 12 also is a pharmaceutical vehicle for parenteral administration, and it is a pharmaceutically acceptable, non-toxic carrier for a beneficial agent, including a drug to be administered to a recipient. The term drug embraces parenterally administrable drug and intravenously administrable drug.

Drip chamber 18 is preferably transparent and in this embodiment it is made of clear glass or plastic. Drip chamber 18 is used to trap air, and it is used in cooperation with regulator clamp 17, for adjusting the rate of flow of medical fluid 12 from reservoir 11 as the flow proceeds dropwise through system 10. Drip chamber 18 is connected through tube 19 to a formulation cell 20.

Formulation cell 20, as seen in FIG. 1, is a cellular unit sized, shaped and structed for use in a parenteral delivery system. Formulation cell 20 is self-contained, self-priming, self-powered and amenable to low cost manufacture. Formulation cell 20 is light-weight and disposable. Formulation cell 20 is provided with a receiving inlet 21 for receiving incoming tube 19, and it is provided also with an outlet 22 for receiving outgoing tube 23. Formulation cell 20 is provided with a wall 24 that surrounds and forms an internal space, not seen in FIG. 1. Formulation cell 20 is closed at end 21 by closure 25 that fits snugly into formulation cell 20, and it is closed at its other end 22 by closure 26. Tubing 23 is connected to a skin-piercing means 27, such as a needle, for administering a fluid agent formulation to a recipient. Formulation cell 20 is made of glass or plastic, preferably of a transparent glass or plastic for viewing its internal contents. Formulation 20 is optionally equipped with an air vent 28.

FIG. 2 depicts formulation cell 20 in opened section with wall 24 opened at 30. In FIG. 2, wall 24 surrounds and defines an internal space 31. Space 31 contains at least one hollow fiber 32, or space 31 contains a multiplicity of hollow fibers 32, that comprise a bundle of hollow fibers. Space 31 can also house spiral wound module discussed in figures presented hereinafter. Hollow fibers 32 are supported at their terminal ends 33 and 34 by passing through and being suitably held by a pair of header support means 35 and 36. Header support means 35 and 36 are joined to the internal surface 37 of wall 24 by means of a suitable adhesive or cement, resin or the like. An adhesive seal also can be used to attach the ends of hollow fibers 32 to header means 35 and 36. Both header means 35 and 36 are seen in FIG. 2, and header 36 means is depicted in cross section. The headers are made of a material substantially impermeable to the passage of a beneficial agent and medical fluid. In this way, the internal space between the headers forms a fluid tight space within formulation cell 20. Each of the hollow fibers 32 in space 31 has the same or about the same length. In a present embodiment, it is generally desirable for the other dimensioned parameters of the hollow fibers, for example, outside diameter and wall 39 thickness to be about the same, although if desired, hollow fibers of different individual diameters and wall thickness can be used for achieving different results. The hollow fibers generally have a uniform bore 40 or lumen, although hollow fibers possessing different bores are within the scope of this invention. Hollow fibers 32 are surrounded in space 31 by beneficial active agent 38, and space 31 also provides sufficient area for fluid 11 and a fluid composition formed in situ in space 31 or beneficial agent solution to pass around the exterior wall surface of the multiplicity of hollow fibers.

In operation, parenteral delivery system 10 of FIG. 1 and its formulation cell 20 as seen in FIG. 2, operate by medical fluid 12 flowing from reservoir 11 through medical tube 16 into drip chamber 18. Medical fluid 12 leaves drip chamber 18 through tube 19 and enters formulation cell 20. In cell 20, fluid 12 flows directly into hollow fibers 32 and outwardly through wall 39 of hollow fiber 32 into space 31. In space 31, fluid 12 mixes with beneficial agent 38 to form a fluid beneficial agent formulation that reenters hollow fiber 32. That is, the agent passes, for example in one embodiment by diffusion, through permeable wall 39 of hollow fiber 32 and enters lumen 40 of said fiber. In another embodiment wall 39 can be formed of a microporous material and the agent can pass through the pores thereof. The fluid agent formulation then flow from cell 20 into tube 23 for administering to a recipient through skin-piercing member 27.

In another embodiment provided by the invention incoming fluid 12 enters hollow fibers 32 and permeates by osmosis through wall 39, particularly when wall 39 is formed of a semipermeable material, into space 31 to dissolve beneficial agent 38 and form an agent solution. The agent solution is then hydrodynamically pumped by osmosis through one or more passageways 36a in header 36. Alternatively, the osmotic pumping process can operate by pumping the drug solution through an optional opening 39a into hollow fiber 32 into lumen 40 and exiting at terminal end 40.

Figure 4:
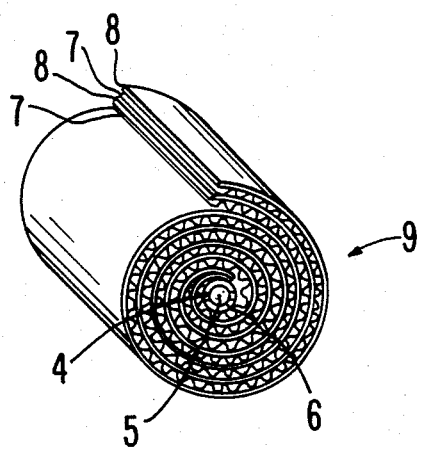
FIG. 4 is a view of the exploded spiral wound membrane-permeation spiral module of FIG. 4.

FIG. 3 illustrates another hollow fiber arrangement that can be housed in formulation cell 20. The hollow fiber arrangement illustrated in FIG. 3 comprises a spiral wound module 9 seen in exploded view. Spiral wound module 9 can be used in those applications wherein it is desirable to maximize the amount of membrane surface that can be placed into the volume available in formulation cell 20. Spiral wound module 9 comprises at least one permselective membrane 8 place in contacting positon with a spacer 7 with membrane 8 and spacer 7 wound around hollow fiber 6 having a lumen 5. Permselective membrane 8 is permeable to the passageway of fluid and it is formed of a permselective diffusional, microporous or a semipermeable material. In an example, permselective membrane 8 can be formed of a microporous poly(urethane) composition. Spacer 7 can be formed of a material impermeable to the passage of agent, such as a cloth. The arrows in the figure indicate the flow of agent through membrane 8 with the permeate passing into hollow fiber 6. The permeate can pass through wall 3, formed of a fluid and agent solution material that permits passage thereof, of fiber 6; or, the permeate can pass through orifice 4 in wall 3 and into lumen 5 of hollow fiber 6. FIG. 4 depicts a spiral wound module 9 in a wound or closed formation with the added feature comprising spacer 7 in a corrugated configuration.

Figure 5:
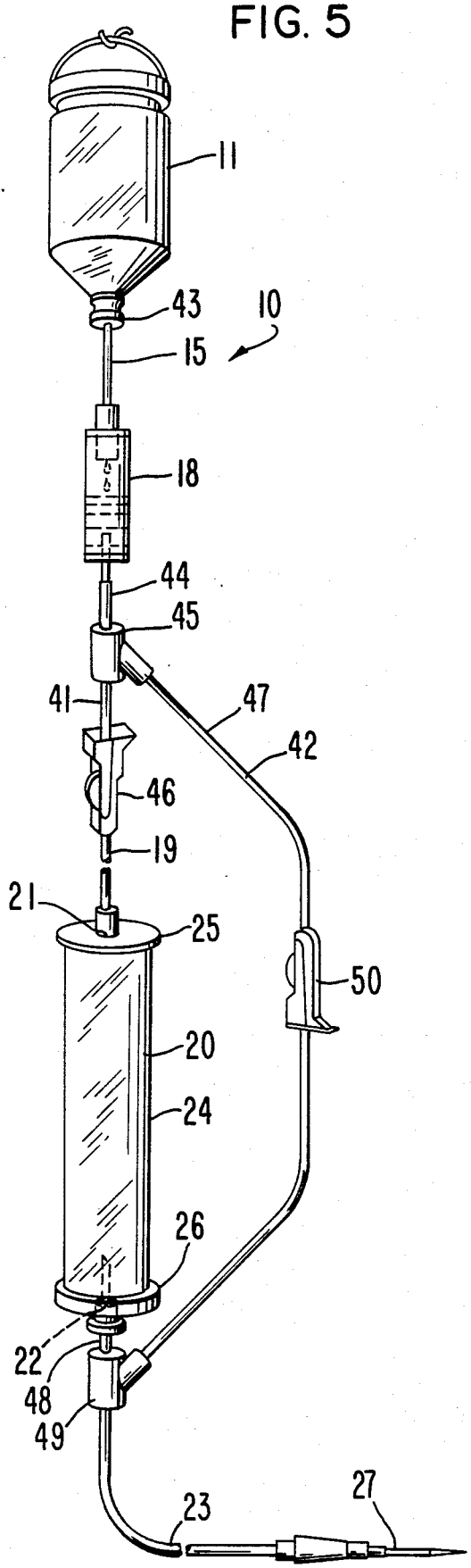
FIG. 5 is a perspective view of another parenteral delivery system provided by the invention comprising a fluid bypass for circumventing fluid flow around a formulation cell; and, FIG. 6 is a perspective view of another parenteral delivery system provided by the invention comprising the formulation cell in a fluid path that circumvents the main fluid flow path.

FIG. 5 represents another parenteral delivery system 10 provided by the invention. The delivery system illustrated is similar to the delivery system depicted in FIGS. 1 and 2. In FIG. 5, parenteral delivery system 10 comprises a primary fluid flow path 41 and a parallel fluid path 42. Primary path 41 comprises reservoir 11 formed as a glass container and suitably capped for serving as a container for a medically acceptable intravenously administrable fluid. Capped end 43 is connected to tube 15 for the flow of fluid into drip chamber 18. Fluid leaves drip chamber 18 through tube 44 connected to one entrance port of a Y-site coupling means 45. The other distant port of coupling means 45 receives tube 19 that passes through flow regulator 46 and connects to formulation cell 20. The other port of coupling means 45 is available for receiving tube 47 of parallel path 42. Fluid entering formulation cell 20 forms therein a fluid agent formulation that leaves cell 20 through tube 48. Tube 48 enters Y-site coupling member 49 that receives outgoing tube 23 for administering the fluid agent formulation to a recipient via delivery means 27. Parallel path 42 comprises tube 47 that passes through flow regulator 50 and enters coupling means 49. Parallel path 42 is a fluid by-pass and it provides a means for letting medical fluid flow by cell 20. This is done, by closing flow regulator 46 and opening regulator 50. The by-pass provides for letting fluid flow through the system directly, without flowing through formulation cell 20, thus administering agent-free fluid to a recipient. The invention illustrated in FIG. 3 provides, by regulating fluid or by regulating fluid agent formulation flow, (a) continuous fluid administration, (b) continuous fluid agent administration, (c) alternating fluid administration and fluid agent administration, and (d) mixing and diluting of fluid and agent administration.

Figure 6:
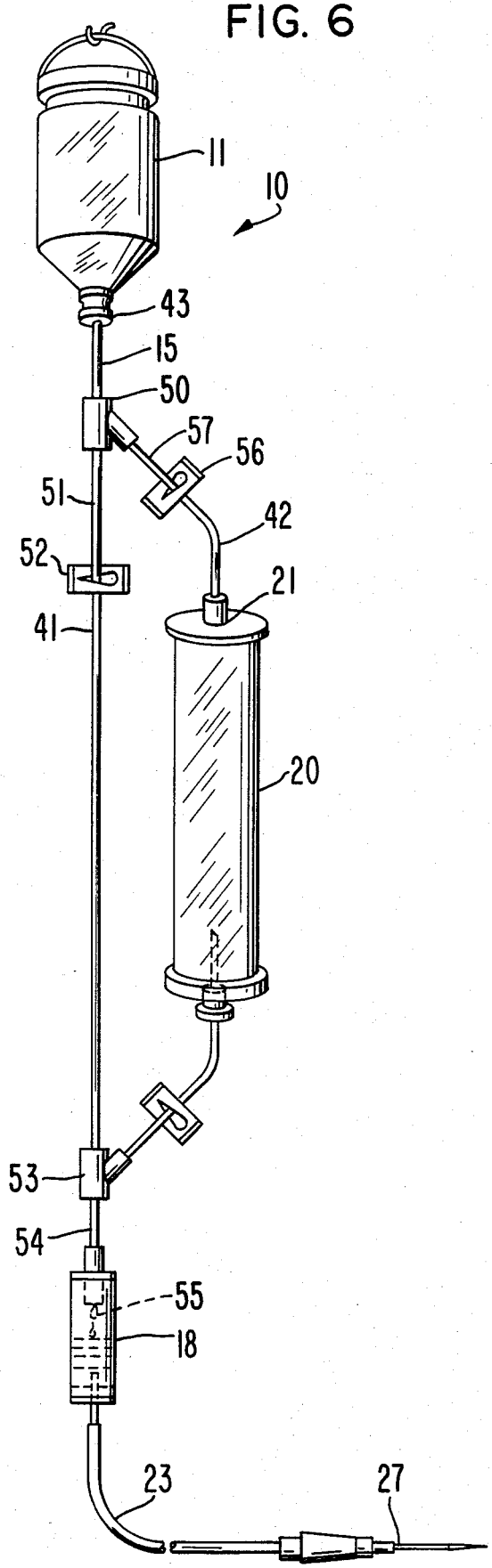

FIG. 6 illustrates another parenteral delivery system provided by the invention. The delivery system illustrated in FIG. 6 uses similar parts as described for FIGS. 1 to 5, and in FIG. 6 they are identified by like numbers. In FIG. 6, parenteral delivery system 10 comprises a primary fluid flow path 41 and a parallel fluid path 42. Primary path 41 comprises reservoir 11 formed of glass or plastic and capped 43 for serving as a container for a medically acceptable intravenously administrable fluid, capped end 43 is connected to a first section of tube 15 leading to a three-way coupling means 50. Fluid passes through coupling means 50 into a second section of medical tubing 51, suitably equipped with a regulatory clamp 52 and then to three-way clamp 53. A third section of medical tube 54 conveys the fluid into drip chamber 18 wherein the flow rate through parenteral delivery system 10 is dropwise regulated for administering through tube 23 and delivery member 27 to a patient. Alternatively, a beneficial agent can be added to the medical fluid by closing clamp 52 and opening clamp 56. These action cause fluid to flow into the parallel path that circumvents the primary path. Parallel path 42 comprises a first section of tubing 57 that passes through clamp 56 and enters receiving end 21 of formulation cell 20. Formulation cell 20 houses the hollow fiber arrangement illustrated in FIG. 2. Fluid containing a beneficial agent leaves formulation cell 20 through a section of tube 58 that passes through a section of tube 58 that passes through open clamp 59. Tube 58 enters coupling means 53, enabling fluid to enter drip chamber 18 and then into tube 23 for administering to a patient through delivery member 27. FIG. 6 provides in both of its operations, continuous or interrupted, and intervals of agent-free administration.

Beneficial agent 38 in formulation cell 20 can be in any pharmaceutical form that leads to a fluid agent formulation by mixing with a parenterally or medically acceptable fluid that enters the cell. The use of formulation cell with agent 38 therein does not require any reconstituting or admixture prior to use. Exemplary pharmaceutically acceptable forms that can be used in cell 20 include solid, microcrystalline, crystalline, particle, pellet, granule, powder, dried, lypophilized and like forms that dissolve, undergo disintegration, and form intravenously administrable solution with a medical fluid. The amount of agent 38 in cell 20, is a dosage unit amount that leads to a preprogrammed, therapeutic or a beneficial effect. The amount thus is a beneficially effective amount of agent that gives a beneficial or a therapeutic result. Formulation cell 20 generally will have a capacity of from about 10 milliliters to 350 milliliters, or more, and it can house from about 0.1 milligrams to 500 grams, or more.

The expression beneficial agent, as used herein, generically denotes any substance that produces a therapeutic or a beneficial result, such as a drug, a carbohydrate, an electrolyte, and the like. Intravenously administrable drugs are known in *Intravenous Medications,* by Sager and Bomar, 1980, published by J. B. Lippincott Co., Philadelphia, Pa. The term fluid or liquid denotes a fluid or a liquid that can be administered parenterally including intravenously, comprising pharmaceutically acceptable carrier for the agent including drug. Exemplary fluids include isotonic saline, Ringer's lactate, and the like. Intravenous fluids are known in *Principles And Practice Of Intravenous Therapy,* by Plumer, 1970, published by Little, Brown and Company, Boston, Mass. The term formulation, and agent formulation as presently used herein, generically indicates the beneficial agent is formulated, mixed, added, dissolved, solubilized and the like into a solution, or carried in or by the fluid into a physical-chemical form acceptable for parenteral including intravenous administration.

Formulation cell 20 containing beneficial agent 38 contains at least one hollow fiber 32, or a multiplicity of hollow fibers, for the fluid agent composition or solution to pass around the exterior wall surface of the hollow fibers, and also for passing through the wall into the lumen of the hollow fibers. The fibers in the cell can be in continous relation to each other. The hollow fibers suitable for use herein, can be diffusional, semipermeable or microporous. Suitable materials for forming the hollow fibers include cellulose esters such as cellulose acetate, cellulose diacetate, cellulose triacetate, cellulose formate, cellulose propionate, cellulose nitrate, and the like; also, mono, di, or tri esters and mixtures of such cellulose esters; cellulose ethers such as methyl, ethyl, hydroxy-alkyl, carboxy-alkyl, and the like; mixed cellulose ethers; regenerated cellulose; acrylonitrile polymers; and the like. The hollow fibers can be prepared by melt, dry, evaporative, and wet spinning procedures using spinnerettes. For example, a fine hollow fiber of cellulose triacetate is readily produced by a wet spinning process in which the ester is dissolved in a solvent, for example acetone or methylene chloride, to form a viscous spinning solution. The spinning solution is extruded into a coagulant bath through the annular spaces in a small annular orifice spinnerette. The extruded fiber coagulates in the desired form of a continously hollow, uniform-walled fiber. Prior to use, the hollow fiber is washed free of any solvent in a bath consisting of water. The fibers generally have, in one presently preferred embodiment an outside diameter of about 10 to 450 microns, and a wall thickness of about 1 to 100 microns. The formulation cell contains at least 1 to $10 \times 10^5$ fibers, or more. Microporous hollow fibers are made from materials such as poly(carbonates), poly(amides), styrene-acrylic acids and its copolymers, poly(sulfones), poly(urethane), and the like. The fibers are made as described and also by using microporous forming procedures, including cooling a solution of flowable polymer below the freezing point whereby solvent evaporates from the solution in the form of crystals dispersed in the polymer and then curing the polymer followed by removing the solvent crystals by cold or hot stretching at low or high temperatures until pores are formed, or by leaching from a polymer a soluble component. Procedures for manufacturing fibers are known in the *Encyclopedia of Chemical Technology,* by Kirk-Othmer, Vol. 12, 1980, published by Wiley-Interscience Co., New York. Header support means 35 and 36, the latter seen in cross-section, are suitably formed of hydrophobic fluid and agent impermeable materials such as poly(fluorotetratethylene), hexafluoropropylene-tetrafluoroethylene copolymer, and the like. Procedures for manufacturing hollow fibers are disclosed in *Industrial Membranes,* by McDermott, 1972, published by Noyes Data Corp., Park Ridge, N.J.

The novel invention uses means for the obtainment of precise control for the formation of fluid agent formulation in a parenteral delivery system. While there has been described and pointed our features of the invention as applied to presently preferred embodiments, those skilled in the art will appreciate that various modifications, changes, additions, and omissions in the parenteral system illustrated and described can be made without parting from the spirit of the invention.

I claim:

1. A method for administrating a beneficial drug to a warm-blooded animal, which method comprises the steps of:
   (a) introducing into the animal a delivery member in fluid communication with an intravenous delivery system, which system comprises:
      (1) a reservoir of a pharmaceutically acceptable fluid;
      (2) a formulation cell in fluid communication with the reservoir, which formulation cell comprises:
         (i) a wall that surrounds a lumen;
         (ii) an inlet in the wall for admitting a fluid into the lumen;
         (iii) a spiral wound module in the lumen, said module comprising a permselective membrane wound around a hollow fiber;
         (iv) a beneficial drug in the lumen in the space formed by the interior surface of the formulation cell and the exterior surface of the formulation cell and the exterior surface of the module;
         (v) an outlet in the wall for letting a fluid drug formulation leave the formulation cell,
   (b) admitting fluid into the formulation cell for contacting the drug in the space that passes into the spiral wound module for entering the hollow fiber to flow from the formulation cell; and,
   (c) administering the fluid drug formulation flowing from the formulation cell to the animal.

2. A parenteral delivery system for administering a beneficial agent to a recipient, the delivery system comprising:
   (a) a reservoir of a medically acceptable fluid; and,
   (b) a formulation cell in fluid communication with the reservoir, the formulation cell comprising:
      (1) a wall that surrounds a lumen;
      (2) an inlet in the wall for letting fluid into the lumen;
      (3) a spiral wound module in the lumen, said module comprising a permselective membrane wound around a hollow fiber;
      (4) a beneficial agent in the space formed by the inside surface of the formulation cell and the outside surface of the module; and
      (5) an outlet in the wall for letting a drug formulation leave the formulation cell.

3. A method for administering a beneficial drug to an animal, which method comprises:
   (a) introducing into the animal a delivery member in fluid communication with an intravenous delivery system, which system comprises:
      (1) a reservoir of a medically acceptable fluid;
      (2) a primary path in fluid communication with the reservoir and the delivery member;
      (3) a circumventing path that permits a fluid to bypass the primary path, said circumventing path comprises:
         (a) a formulation cell, which formulation cell comprises:
            (i) a wall that surrounds an internal lumen;
            (ii) an inlet in the wall for letting fluid into the lumen;
            (iii) a spiral wound module in the lumen, the module comprising a permselective membrane wound around a hollow fiber;
            (iv) a beneficial drug in the lumen in the space between the module and the inside surface of the wall of the lumen;
            (v) an outlet in the wall for letting fluid and drug leave the formulation cell;
      (b) admitting fluid into the formulation cell for contacting the drug to form a fluid drug formulation that passes into the spiral wound module for entering the hollow fiber for flowing from the formulation cell; and,
      (c) administering the fluid drug formulation flowing from the formulation cell to the animal.

4. A parenteral delivery system for administering a beneficial agent to a recipient, the delivery system comprising:
   (a) a reservoir of a medically acceptable fluid;
   (b) a primary fluid path in fluid communication with the reservoir;
   (c) a circumventing path that permits a fluid to circumvent the primary path, said circumvention path comprising:
      (1) a formulation cell, the cell comprising:
         (i) a wall that surrounds a lumen;
         (ii) an inlet in the wall for letting fluid into the lumen;
         (iii) a spiral wound module in the lumen, the module comprising at least one membrane that permits the passage of fluid and agent wound about a hollow fiber; and,
         (iv) a beneficial agent in the lumen in the space defined by the inside of the wall and the module; and,
         (v) an outlet in the wall for letting drug and fluid exit the formulation cell.

5. A formulation cell for use with an intravenous delivery system, the formulation cell comprising;
   (a) a wall that surrounds an internal lumen;
   (b) an inlet in the wall for letting fluid enter the lumen;
   (c) a spiral module in the lumen, said module comprising at least one membrane that permits the passage of fluid and a beneficial agent spiral wound around a hollow fiber;
   (d) a beneficial agent acceptable for intravenous delivery in the cell between the wall and the space surrounding the module; and,
   (e) a outlet in the wall for letting agent and fluid exit the module.

* * * * *